United States Patent
Ott

(10) Patent No.: US 6,448,418 B1
(45) Date of Patent: Sep. 10, 2002

(54) METHOD OF EPOXIDIZING OLEFINS

(75) Inventor: Christian Ott, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/807,449

(22) PCT Filed: Oct. 26, 1999

(86) PCT No.: PCT/EP99/08079

§ 371 (c)(1),
(2), (4) Date: Apr. 25, 2001

(87) PCT Pub. No.: WO00/24726

PCT Pub. Date: May 4, 2000

(30) Foreign Application Priority Data

Oct. 27, 1998 (DE) .......................... 198 49 527

(51) Int. Cl.⁷ ............................. C07D 301/16
(52) U.S. Cl. ....................... 549/526; 549/527
(58) Field of Search ................ 549/519, 527, 549/526

(56) References Cited

U.S. PATENT DOCUMENTS 4,584,390 A    4/1986   Dieckelmann et al.

FOREIGN PATENT DOCUMENTS

| CA | 2222495    | 11/1997 |
|----|------------|---------|
| DE | 1 230 005  | 12/1966 |
| DE | 195 19 887 | 6/1996  |
| EP | 0 032 989  | 8/1981  |
| GB | 1048318    | 11/1966 |

*Primary Examiner*—T. A. Solola
(74) *Attorney, Agent, or Firm*—Oblon, Spivak, McClelland, Maier & Neustadt, P.C.

(57) ABSTRACT

A process is provided for the epoxidation of olefins with percarboxylic acid in a reaction mixture consisting of an aqueous phase and an organic phase, the percarboxylic acid being formed in situ in the aqueous phase from hydrogen peroxide and a carboxylic acid or a carboxylic anhydride, and the olefins being dissolved in an organic solvent in the organic phase, wherein the epoxidation is carried out in several steps, each step being carried out with a fresh aqueous phase and the aqueous phase being separated off after each step.

11 Claims, No Drawings

METHOD OF EPOXIDIZING OLEFINS

This application is a 371 of PCT/EP99/08079 filed Oct. 26, 1999.

The invention relates to a process for the epoxidation of olefins in a two-phase reaction system with percarboxylic acids formed in situ.

Epoxides of olefinically unsaturated compounds represent an important class of intermediates. In a process known for a long time, olefins are epoxidized by reaction with percarboxylic acids, which can be produced in situ from hydrogen peroxide and carboxylic acids. By scission, the oxiran ring formed in place of the olefinic double bond can react with a large number of compounds containing active hydrogen, thereby opening up an extensive secondary chemistry.

In the processes of the state of the art, the reactivity of epoxides results in the formation of by-products. Thus epoxides react in the presence of water and carboxylic acids to give glycols or their mono- and diester, the scission of the oxiran ring being acid-catalyzed. The problem here is that the formation of the percarboxylic acid is also acid-catalyzed, so the process is often carried out in the presence of mineral acids as catalysts.

DE-B 1 230 005 discloses a process for the epoxidation of linear alpha-olefins which uses peracetic acid free of water and mineral acid as the epoxidizing reagent and is carried out in the presence of an inert solvent such as acetone, methyl acetate or ethyl acetate. The disadvantages are the long reaction times of several hours, the incomplete olefin conversion and the high proportion of by-products, especially glycol monoester. Also, the epoxidizing reagent used is expensive.

DE-C 195 19 887 describes a process for the epoxidation of olefinically unsaturated compounds with percarboxylic acid prepared in situ, said process being carried out with water as the only solvent and in the presence of inhibitors. No information is given on the exact composition of the product mixture.

DE-A 15 68 016 discloses a process in which alpha-olefins are epoxidized in a water-immiscible solvent with a percarboxylic acid formed in situ in the aqueous phase, the reaction mixture being stirred in such a way as to maintain a single phase interface. This procedure demands very long reaction times.

EP-A 0 032 989 describes a process for the epoxidation of alpha-olefins with performic acid formed in situ, said process being carried out in the absence of a solvent and an acid catalyst. Epoxidation by this process demands a long overall reaction time. Also, the olefin conversion is unsatisfactory despite the long reaction time.

It is an object of the present invention to provide a process for the epoxidation of olefins in which a quantitative conversion is achieved and products of high purity are obtained after short reaction times.

We have found that this object is achieved by a process for the epoxidation of olefins with percarboxylic acid in a reaction mixture consisting of an aqueous phase and an organic phase, the percarboxylic acid being formed in situ in the aqueous phase from hydrogen peroxide and a carboxylic acid or a carboxylic anhydride, and the olefins being dissolved in an organic solvent in the organic phase. The process according to the invention comprises carrying out the epoxidation in several steps, each step being carried out with a fresh aqueous phase and the aqueous phase being separated off after each step.

In terms of the present invention, olefins are compounds containing one or more olefinic double bonds. Examples of compounds with olefinic double bonds are linear or branched mono- and diolefins having from 6 to 30 C atoms, unsaturated, optionally hydroxy-substituted fatty acids having from 6 to 24 C atoms and from 1 to 5 double bonds, their esters or triglycerides, and unsaturated alcohols having from 6 to 24 C atoms and from 1 to 3 double bonds. Polyalkenes and terpenes are also olefins in terms of the present invention. In addition to the double bond(s), the olefins can contain other functional groups which do not react, or react only slowly, with the solvent or the epoxidizing reagent under the reaction conditions. For example, the olefins can contain heteroatoms, such as an ether oxygen, or can be substituted by hydroxyl groups, carboxylic acid groups, carboxamide, carboximide, carboxylic acid ester, lactam or lactone groups, aromatic radicals or halogen atoms. The olefin used may already contain epoxy groups, keto groups or cyclic carbonate groups.

Examples of suitable olefins are mono- or diolefins having from 6 to 30 C atoms, preferably from 10 to 24 C atoms and particularly preferably from 12 to 18 C atoms, which can be branched or unbranched. Branched olefins can also be branched on the double bonds. Both cis and trans isomers can be used. Examples are 1-hexene, 2-hexene, 3-hexene, 1,3-hexadiene, 1,4-hexadiene, 3-methyl-1,3-pentadiene, 2-methyl-1-pentene, 3,3-dimethyl-1-butene, 1-heptene, 3-heptene, 1-octene, 4-octene, 1-nonene, 1-decene, 1-undecene, 1-dodecene, 1-tetradecene, 1-hexadecene, 1-octadecene. The preferred olefins are linear, for example the linear olefins mentioned above, of which those with a terminal double bond (linear alpha-olefins) are particularly preferred. Of the linear alpha-olefins, those with an even number of C atoms are particularly preferred because of their ready availability from petrochemical processes.

Other suitable olefins are cyclic olefins such as cyclohexene, cyclooctene, cyclooctadiene, cyclodecene and cyclododecene, and their substituted derivatives, for example substituted cyclohexenes such as 1,3-dimethylcyclohexene, 1,4-dimethylcyclohexene or 1-ethylcyclohexene.

Other suitable olefins are terpenes, terpene alcohols and other natural substances with one or more double bonds, such as steroids. In addition to the olefinic double bonds, these can contain other functional groups such as hydroxyl or keto groups. Examples are 2-carene, delta-3-carene, alpha-pinene, beta-pinene, verbenol, myrtenol, cis-jasmone, dihydrocarveol, alpha-terpinene, gamma-terpinene, alpha-ionone, beta-ionone, limonene, carvone, citronellic acid, trans-vaccenic acid, geraniol, farnesol, phytol, citronellol, ergosterol, myrcene, squalene and camphene.

Other suitable olefins are unsaturated fatty acids having from 6 to 24 C atoms and from 1 to 5 double bonds, which can optionally be substituted by hydroxyl groups, for example oleic acid, elaidic acid, linoleic acid, linolenic acid, arachidonic acid, linolenelaidic acid, linoelaidic acid, myristoleic acid, palmitoleic acid, undecenoic acid or ricinoleic acid. Other suitable olefins are the esters of unsaturated fatty acids, especially their triglycerides such as those which occur in animal and vegetable fats and oils, for example in soya oil, sunflower oil, linseed oil, rapeseed oil, colza oil, groundnut oil, palm oil, coconut oil, castor oil, tallow, lard and fish oil. Other suitable olefins are unsaturated fatty alcohols having from 1 to 3 double bonds, such as oleyl alcohol, elaidyl alcohol, linoleyl alcohol, linolenyl alcohol and arachidonyl alcohol.

Other preferred olefins are polyalkylenes such as polyisobutene.

The olefins are dissolved in an organic solvent. Suitable organic solvents form a two-phase reaction system with the epoxidizing reagent consisting of a carboxylic acid and aqueous hydrogen peroxide solution, so they are water-immiscible organic solvents or organic solvents having only a limited miscibility with water. The organic solvents are used in an amount appropriate for the formation of an organic phase separated from the aqueous phase. Solvents which are completely miscible with water are therefore unsuitable.

Preferred organic solvents are also inert toward aqueous hydrogen peroxide solution, carboxylic acids and percarboxylic acids and especially toward the epoxides formed. Preferred solvents have a markedly different density from that of water, hydrogen peroxide solution or the aqueous carboxylic acid solution.

Preferred organic solvents have at least a limited miscibility with water. The water absorption capacity of the organic solvent at 25° C. is preferably at least 0.1 and at most 10 mol %, particularly preferably at least 0.1 and at most 5 mol %, very particularly preferably at least 0.2 and at most 2 mol % and especially at least 0.2 and at most 1.0 mol %.

Examples of suitable solvents are aliphatic and aromatic hydrocarbons and halogenohydrocarbons such as pentanes, hexanes, heptanes, octanes, cyclopentane, cyclohexane, methylcyclopentane, methylcyclohexane, dichloromethane, chloroform, carbon tetrachloride, trichloroethane, benzene, toluene, xylenes, ethylbenzene, chlorobenzene and dichlorobenzenes, and also aliphatic and alicyclic ethers such as diethyl ether, dipropyl ether, diisopropyl ether, tetrahydrofuran and dioxane. Aromatic hydrocarbons such as benzene, chlorobenzene, toluene, ortho-, meta- and para-xylene and ethylbenzene, and halogenohydrocarbons such as dichloromethane, chloroform and chlorobenzene, are particularly preferred because their water absorption capacity is sufficiently high but limited and their reactivity is low. The weight ratio of olefin to solvent generally ranges from 1:100 to 10:1, preferably from 1:10 to 2:1 and particularly preferably from 1:5 to 1:1.

The percarboxylic acid is formed in situ in the aqueous phase from a carboxylic acid or a carboxylic anhydride and aqueous hydrogen peroxide solution.

Suitable carboxylic acids are those which are at least partially soluble in the aqueous phase at the reaction temperature, such as at least partially water-miscible aliphatic, araliphatic and aromatic carboxylic acids. Examples are formic acid, acetic acid, chloroacetic acid, dichloroacetic acid, trichloroacetic acid, phenylacetic acid, trifluoroacetic acid, propionic acid, benzoic acid, meta-chlorobenzoic acid and phthalic acid. It is also possible to use carboxylic anhydrides, for example maleic anhydride. Preferred carboxylic acids have a high solubility in water and a low solubility in the organic solvents used. Particularly preferred carboxylic acids are miscible with water in all proportions. Examples of preferred carboxylic acids are aliphatic carboxylic acids having from 1 to 3 C atoms, such as formic acid, acetic acid and propionic acid. Maleic anhydride is also preferred. Acetic acid and formic acid are particularly preferred and formic acid is very particularly preferred.

The hydrogen peroxide solution used is generally an aqueous hydrogen peroxide solution with a concentration of 3 to 95% by weight, preferably of 10 to 90% by weight, particularly preferably of 30 to 85% by weight and especially of 50 to 80% by weight.

The epoxidation is carried out in several steps, a fresh aqueous phase being used in each step. In each individual step, it is possible to introduce the full amount of carboxylic acid all at once or to introduce only part of the carboxylic acid and, where appropriate, to add the remainder of the carboxylic acid and the hydrogen peroxide solution in portions or continuously. The first variant is the preferred procedure, it being particularly preferred to introduce the full amount of carboxylic acid and to run the hydrogen peroxide solution in continuously. The aqueous phase is dispersed as droplets in the organic phase in each step, preferably by stirring.

The molar ratio of the amounts of hydrogen peroxide and carboxylic acid used per step (based on monocarboxylic acids) generally ranges from 100:1 to 1:10, preferably from 10:1 to 1:2, particularly preferably from 5:1 to 1:2 and very particularly preferably from 2:1 to 1:2. This ratio can differ from step to step.

The molar ratio of the total amount of hydrogen peroxide used in all the steps to the amount of olefin used is generally at least stoichiometric, i.e. (based on monoolefins) at least 1:1, preferably 5:1 to 1:1 and particularly preferably 2:1 to 1:1.

The epoxidation is carried out preferably in two to four steps and particularly preferably in three or four steps. The amount of hydrogen peroxide used per step can be the same or different. Preferably, the amount of hydrogen peroxide used per step will decrease with increasing olefin conversion. The amount of carboxylic acid used per step can also be the same or different. Preferably, the amount of carboxylic acid used per step will decrease from step to step with increasing olefin conversion, especially when the amount of hydrogen peroxide used per step also decreases from step to step.

In one preferred embodiment of the process according to the invention, the amount of hydrogen peroxide used in the first step will be stoichiometric, based on olefin, i.e. one mol of hydrogen peroxide per mol of olefinic double bonds, and in every other step will be smaller but in total not more than two mol and particularly preferably not more than 1.5 mol.

In another preferred embodiment, the amount of hydrogen peroxide used in the first step will be substoichiometric, based on olefin, preferably 0.5 mol of hydrogen peroxide per mol of olefinic double bond, and in every other step will be smaller but in total not more than 1.5 mol and particularly preferably not more than 1.2 mol.

In another preferred embodiment, the epoxidation is carried out in such a way that generally 30 to 90% and preferably 30 to 70% of the olefin has been converted after the first step. If the process according to the invention is carried out in at least three steps, the olefin conversion is generally 50 to 95% and preferably 60 to 90% after the second step. The progress of the reaction can be monitored by gas chromatography or titrimetry, for example by determining the iodine number or the epoxy content, and an epoxidation step can be interrupted by phase separation when a particular conversion is reached.

After each step, the aqueous phase is separated off and replaced with a fresh aqueous phase. It is not absolutely necessary here for the percarboxylic acid and/or hydrogen peroxide to have reacted completely, although this is desirable if the peracid is to be utilized efficiently.

The epoxidation reaction is preferably carried out under atmospheric pressure. The reaction temperature depends on the chain length of the olefin and is generally 60 to 100° C. The reaction can be carried out in conventional reaction apparatuses, such as a stirred tank or stirred tank cascade, with conventional phase separation devices. The reaction is preferably carried out under reflux, the condenser used ensuring adequate heat dissipation.

The process according to the invention has a number of advantages. Thus the total duration of the epoxidation reaction is short, being generally <10 h, preferably <7 h and particularly preferably <5 h for an olefin conversion of at least 95% by weight, preferably of at least 98% by weight. The reaction time is preferably <1 h per step.

An epoxide of high purity is formed in the process according to the invention. The epoxy content of the crude product is generally >90 mol %, preferably >95 mol %, based on the olefin used. The glycol content is generally <5% by weight, preferably <2% by weight, and the total content of other secondary constituents, such as the glycol monoesters and diesters of the carboxylic acids used, is generally <5 mol %, preferably <2 mol %.

Changing the aqueous phase maintains a sufficiently high carboxylic acid concentration and hydrogen peroxide concentration in the aqueous phase to avoid the use of mineral acids as catalysts for formation of the peroxide.

On the one hand, carrying out the process in a two-phase reaction system substantially suppresses secondary reactions of the epoxides present in the organic phase with water or the carboxylic acid present in the aqueous phase, for example the acid-catalyzed scission of the oxiran ring to form glycols, monoesters and diesters. The risk of forming by-products can be further lowered by reducing the amount of carboxylic acid in the aqueous phase as the olefin conversion progresses.

On the other hand, choosing a suitable solvent of sufficiently high polarity (water absorption capacity) ensures effective transport of the percarboxylic acid into the organic phase and hence a sufficiently high reaction rate.

The product obtained can be used without further purification, if appropriate after distillation of the solvent. When using e.g. toluene as the organic solvent and formic acid as the carboxylic acid, any traces of formic acid and water are entrained out as an azeotrope to give a substantially dry and acid-free product. The same applies to the systems toluene/ acetic acid/water, xylene/acetic acid/water, xylene/ formic acid/water and dichloromethane/formic acid/water. If very high demands are made on product purity, it is possible to carry out a fine distillation under reduced pressure.

The invention is illustrated in greater detail by means of the examples which follow.

EXAMPLES

Example 1

336 g of 1-dodecene (2.0 mol), 800 g of toluene and 46 g of concentrated formic acid (99% by weight, 1.0 mol) are placed in a 2 l flask and heated to 90° C. In a first step, 136 g of hydrogen peroxide solution (50% by weight, 2.0 mol) are added dropwise over a period of 20 min to the intensely stirred mixture and stirring is then continued for a further 20 min. The aqueous phase is separated off. In the second to fourth steps, the indicated amounts of formic acid are added all at once and the indicated amounts of hydrogen peroxide (concentrations and temperature as above) are added dropwise over a period of 5 min in each step, stirring is continued for 20 min in each step and the aqueous phase is then separated off.

2nd step: 0.5 mol of formic acid and 0.5 mol of hydrogen peroxide; 3rd and 4th steps: in each case 0.3 mol of formic acid and 0.3 mol of hydrogen peroxide.

This gives a crude product of the following composition (in GC area %): 1,2-epoxydodecane 93.2%, 1-dodecene 1.1%, 1,2-dodecanediol 2.1%, 1,2-dodecanediol monoformyl ester and 1,2-dodecanediol diformyl ester 1.6%.

Example 2

168 g of 1-dodecene (1.0 mol), 400 g of dichloromethane and 96 g of concentrated formic acid (99% by weight, 1.5 mol) are placed in a 1 l flask and heated to 90° C. In a first step, 102 g of hydrogen peroxide solution (50% by weight, 1.5 mol) are added dropwise over a period of 5 min to the intensely stirred mixture and stirring is then continued for a further 45 min. The aqueous phase is separated off. In the second and third steps, the indicated amounts of formic acid are added all at once and the indicated amounts of hydrogen peroxide (concentrations and temperature as above) are added dropwise over a period of 5 min in each step, stirring is continued for 45 min in each step and the aqueous phase is then separated off.

2nd step: 0.5 mol of formic acid and 0.5 mol of hydrogen peroxide; 3rd step: 0.3 mol of formic acid and 0.3 mol of hydrogen peroxide. This gives a crude product containing 94.5% by weight of 1,2-epoxydodecane.

Example 3

2295.3 g of polyisobutene 1000 (3.0 mol), 1200 g of toluene and 92 g of concentrated formic acid (99% by weight, 2.0 mol) are placed in a 5 l flask and heated to 90° C. In a first step, 136 g of hydrogen peroxide solution (50% by weight, 2.0 mol) are added dropwise over a period of 40 min to the intensely stirred mixture and stirring is then continued for a further 45 min. The aqueous phase is separated off. In the second step, 0.5 mol of formic acid is added all at once, 0.5 mol of hydrogen peroxide (concentrations and temperature as above) is added dropwise over a period of 20 min, stirring is continued for 60 min and the aqueous phase is then separated off to give the epoxide in quantitative yield.

Example 4

2295.3 g of polyisobutene 1000 (3.0 mol), 1200 g of toluene and 92 g of concentrated formic acid (99% by weight, 2.0 mol) are placed in a 5 l reactor and heated to 90° C. In a first step, 136 g of hydrogen peroxide solution (50% by weight, 2.0 mol) are added dropwise over a period of 40 min to the intensely stirred mixture and stirring is then continued for a further 60 min. The aqueous phase is separated off. In the second step, 46 g (1.0 mol) of formic acid are added all at once, 68 g (1.0 mol) of hydrogen peroxide (concentrations and temperature as above) are added dropwise over a period of 20 min, stirring is continued for 60 min, the aqueous phase is then separated off and the organic phase is concentrated under reduced pressure to give the epoxide in quantitative yield.

Example 5

2295.3 g of polyisobutene 1000 (3.0 mol), 983.7 g of Mihagol®M (a mixture of $C_{10}$-$C_{14}$ n-paraffins) and 92 g of concentrated formic acid (99% by weight, 2.0 mol) are placed in a 10 l reactor and heated to 90° C. In a first step, 136 g of hydrogen peroxide solution (50% by weight, 2.0 mol) are added dropwise over a period of 20 min to the intensely stirred mixture and stirring is then continued for a further 60 min. The aqueous phase is separated off. In the second step, 46 g (1.0 mol) of formic acid are added all at once, 1.0 mol of hydrogen peroxide (concentrations and temperature as above) is added dropwise over a period of 10 min, stirring is continued for 60 min and the aqueous phase is then separated off. 300 ml of toluene are then added to the organic phase, and water and formic acid are removed by distillation. Finally, the organic phase is concentrated under reduced pressure to give the epoxide in quantitative yield.

Comparative Example C1

168 g of 1-dodecene (1.0 mol) are mixed with 92 g of concentrated formic acid (99% by weight, 2.0 mol). 81.6 g of hydrogen peroxide (50% by weight, 1.2 mol) are added dropwise at 90° C. over a period of 15 min to the intensely stirred mixture and intense stirring is then continued at 90° C. for a further 2 h. The course of the reaction is monitored by titration of the amount of peracid/peroxide. When the reaction has ended, the phases are separated at 80° C. and the organic phase is analyzed by gas chromatography.

209 g of a low-melting colorless solid of the following composition (in GC area %) are obtained: 1,2-dodecanediol 73.4%, 1,2-dodecanediol 1-monoformyl ester 9.8%, 1,2-dodecanediol 2-monoformyl ester 15.9%, 1,2-dodecanediol diformyl ester 0.9%.

We claim:

1. A process for the epoxidation of olefins with percarboxylic acid in a reaction mixture consisting of an aqueous phase and an organic phase, the percarboxylic acid being formed in situ in the aqueous phase from hydrogen peroxide and a carboxylic acid or a carboxylic anhydride, and the olefins being dissolved in an organic solvent in the organic phase, which process comprises carrying out the epoxidation in several steps, each step being carried out with a fresh aqueous phase and the aqueous phase being separated off after each step.

2. A process as claimed in claim 1, wherein the water absorption capacity of the organic solvent at 25° C. is at least 0.1 and at most 10 mol %.

3. A process as claimed in claim 1, wherein the organic solvent is selected from benzene, toluene, ortho-, meta- and para-xylene, ethylbenzene and halogenhydrocarbons.

4. A process as claimed in claim 1, wherein the carboxylic acid or carboxylic anhydride is selected from formic acid, acetic acid, propionic acid and maleic anhydride.

5. A process as claimed in claim 1, wherein the carboxylic acid is formic acid.

6. A process as claimed in claim 1, wherein linear alpha-olefins having from 6 to 30 C atoms are epoxidized.

7. A process as claimed in claim 1, wherein the amount of hydrogen peroxide used per step decreases from step to step.

8. A process as claimed in claim 1, wherein the amount of acid used per step decreases from step to step.

9. A process as claimed in claim 1, wherein the epoxidation is carried out in at least three steps in such a way that the olefin conversion is 30 to 70% after the first step and 50 to 90% after the second step.

10. A process as claimed in claim 1, wherein the epoxidation is carried out under atmospheric pressure and at a temperature of 60 to 100° C.

11. A process as claimed in claim 1, wherein polyisobutene is epoxidized.

* * * * *